United States Patent [19]

Kaufman

[11] 4,269,851

[45] May 26, 1981

[54] 8-AMINOALKYL-4-ALKYLPSORALENS

[75] Inventor: Kurt D. Kaufman, Kalamazoo, Mich.

[73] Assignee: Thomas C. Elder, Inc., Hamilton, Ind.

[21] Appl. No.: 73,907

[22] Filed: Sep. 10, 1979

[51] Int. Cl.³ ............... C07D 493/04; A61K 31/365
[52] U.S. Cl. ............................. 424/279; 260/343.21
[58] Field of Search ................. 260/343.21; 424/279, 424/59

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 260/343.21 |
| 4,217,445 | 8/1980 | Nikolaiski | 260/343.21 |

OTHER PUBLICATIONS

Hearst et al., (II), Chem. Abst. 87: 78962f, 1977.
Dawber, J. Soc. Comet. Chem., 28–403–406, 1977.
Martins et al., Chem. Abst., vol. 81, 1974, 99676g.
Shen et al., Chem. Abst., vol. 88, 88: 59494j.
Johnston et al., Chem. Abst., 87: 147284a.
Isaacs et al., Chem. Abst., 86: 135108n.

*Primary Examiner*—Henry R. Jiles
*Assistant Examiner*—Jane T. Fan
*Attorney, Agent, or Firm*—Gordon W. Hueschen

[57] ABSTRACT

The invention relates to 8-aminoalkyl-4-alkylpsoralens having enhanced photosensitizing activity, especially oral activity, including early onset, increased maximum, and rapid decline, as well as low toxicity, when compared with psoralens of different structure.

9 Claims, No Drawings

8-AMINOALKYL-4-ALKYLPSORALENS

BACKGROUND OF THE INVENTION

1. Field of Invention

Psoralens, photochemotherapy, psoralens having enhanced photosensitizing activity for use in photochemotherapy.

2. Prior Art

Psoralens have been used for years as dermalphotosensitizing agents, e.g., in the treatment of vitiligo. Their topical and/or oral application, followed by irradiation with light, results in stimulation of melanin, thus producing a tanning effect. They have accordingly also been used for such cosmetic purpose. More recently, psoralens have been found useful in the photochemotherapeutic treatment of psoriasis, in which case they are administered orally or topically to the subject, whose skin is subsequently exposed to controlled ultraviolet radiation, as in a Psoralite (TM) apparatus. A high percentage of remissions of this disease have been effected in such manner.

The effectiveness of a psoralen for such uses and for such purpose is related to its ability to produce erythema upon the skin upon irradiation. Psoralens also have other uses, and their uses, as well as underlying rationale and theory, are partially elucidated in U.S. Pat. No. 4,124,598, and are otherwise well-known in the art from various preexisting publications.

With the increasing emphasis on photochemotherapeutic treatments for various purposes using psoralens and controlled application of ultraviolet light, the requirements for optimally-effective photosensitizing psoralens have become more apparent. To eliminate the necessity of excessive and perhaps dangerous ultraviolet light applications or dosages, maximum photosensitization is one obvious criterion. However, to eliminate excessive periods of waiting before photochemotherapy can be commenced, rapid onset of photosensitization upon topical or oral administration of the photosensitizing agent is also of significance. Perhaps an even more important criterion is rapid decline in photosensitizing activity of the photosensitizing agent after reaching maximum and/or effective photosensitization levels after administration. Obviously, if the photosensitization effect does not decline relatively rapidly, or at least within a reasonably limited period after maximization, a patient must be confined for uneconomic and undesirable periods after treatment so that photosensitization does not continue after the desired ultraviolet light treatment period, with the distinct danger of excessive and undesirable continuance of photochemotherapy because of exposure to normally-encountered light rays upon leaving the treatment area. Thus, the criteria of rapid onset, early maximization, and rapid decline of photosensitization effect have already become established as desirable criteria for the photosensitizing agent in this relatively new but rapidly-expanding field of photochemotherapy, certainly of equal importance as contrasted to the single previously-important criterion of high maximum photosensitization activity alone.

Although some psoralens, such as trimethylpsoralen (4,5', 8-trimethylpsoralen or trioxsalen) are characterized by considerable topical activity, they have a diminished order of oral activity, or at least the oral activity is a modicum for purposes of practical photochemotherapeutic utilization. In contrast, 8-methoxypsoralen is characterized by significant oral activity. The psoralen compounds of U.S. Pat. Nos. 4,124,598 and 4,130,568 are also characterized structurally by the presence of an 8 carbon atom substituent, e.g., an 8-methoxy or 8-methyl substituent, which has heretofore apparently been considered desirable for substantial photosensitizing activity, whether oral or topical of course along with other substituents present in the 4',4, and 5' positions, in those prior art psoralen compounds which have heretofore been found to have desired photochemotherapeutic activity.

OBJECTS OF THE INVENTION

It is an object of the invention to provide novel psoralen compounds. It is a further object to provide novel psoralen compounds which have enhanced characteristics when compared with psoralen compounds of different structure. It is an additional object to provide novel psoralen compounds having enhanced photosensitizing characteristics in accord with the foregoing stated criteria. It is a still further object to provide novel psoralen compounds having enhanced photosensitizing characteristics and relatively low toxicity, and of a structure differing essentially from known psoralen compounds, the advantageous properties of which could not be predicted on a basis of any known structure-activity relationships. Still other objects will be apparent to one skilled in the art and still additional objects will become apparent hereinafter from the following description and claims.

SUMMARY OF THE INVENTION

The present invention relates to 8-aminoalkyl-4-alkylpsoralens having enhanced photosensitizing activity, especially oral activity, including early onset, increased maximum, and rapid decline, as well as low toxicity, when compared with psoralens of different structure. It is particularly concerned with 4-loweralkyl-8-primaryaminoloweralkylpsoralens, particularly 4-loweralkyl-8-aminomethylpsoralens, and especially 4-methyl-8-aminomethylpsoralen. It is to be noted that the compounds of this invention have no 8 carbon atom methyl or methoxy substituent as in the prior art compounds trisoralen (4,5',8-trimethylpsoralen), 8-methoxypsoralen, or the compounds of U.S. Pat. Nos. 4,124,598 or 4,130,568. No. 4' or 5' carbon atom substituent is essential, as in U.S. Pat. No. 4,124,598. An 8-aminoloweralkyl group is uniquely present, however, which is absent from all the aforementioned reference compounds. These new compounds are characterized by excellent photosensitization activity according to the aforesaid various criteria, as well as relatively low toxicity.

The compounds of the invention have the formula:

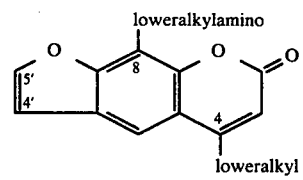

4-loweralkyl-8-primaryaminoloweralkylpsoralen, wherein loweralkyl is preferably methyl.

DETAILED DESCRIPTION OF THE INVENTION

The following preparations and Examples are given by way of illustration only.

Starting 4,8-dialkylpsoralens and their method of preparation are known. Caporale and Bareggi, Gazz. Chim. Ital, 98, 444–457 (1968). Their preparation is from known 7-allyloxy-4,8-dialkylcoumarins via 6-allyl-7-hydroxy-4,8-dialkylcoumarins, also known compounds having a known method of preparation. Rangaswami and Seshadri, Proc. Indian Acad, Sci. 7A, 8-12 (1938). According to the invention, variations in the alkyl groups in the end product are effected by variations in the starting 4,8-dialkylpsoralen, other reaction steps remaining the same.

Thin layer chromatography was done on Analtech, Silica Gel$_{254}$ 250 micron, glass-backed, slides using benzene:2-butanone::17:3. NMR were run on a Perkin Elmer Model R-24B. All melting points are uncorrected.

4-METHYL-8-AMINOMETHYLPSORALEN

7-Allyloxy-4,8-dimethylcoumarin. 7-Hydroxy-4,8-dimethylcoumarin (91.075 g, 0.479 mol), anhydrous $K_2CO_3$ (302.9 g, 2.190 mol), and allyl bromide (217.1 mL, 2.51 mol) were added to 2.5 L of reagent grade acetone. The milky mixture was refluxed for eight hours with overhead stirring, filtered, and the filtrate was concentrated to dryness with the rotary evaporator to obtain 7-allyloxy-4,8-dimethylcoumarin (113.5 g, 0.493 mol, 103%). The crude product melted at 94.0°–100° C. (lit. mp 108° C.) and was used in the next step.

6-Allyl-7-hydroxy-4,8-dimethylcoumarin. Crude 7-allyloxy-4,8-dimethylcoumarin (113.4 g, 0.493 mol) was dissolved in 600 mL diethyl aniline with heating, and the solution was allowed to reflux for two hours. After the solution had cooled and some product had precipitated, petroleum ether (b.p. 30°–60° C., 1200 mL) was added and a white precipitate was collected by filtration and recrystallized from 650 mL of 95% EtOH to obtain colorless crystals (38.88 g, 0.204 mol, 41%) of mp 166.0°–167.0° C. (lit mp 168°–170° C.).

4,8-Dimethylpsoralen. 6-Allyl-7-hydroxy-4,8-dimethylcoumarin (23.00 g, 0.1 mol), and $KIO_4$ (54 g, 0.23 mol) were added to 650 mL of methanol. To this mixture was added $OsO_4$ (1.00 g, 3.93 mmol) dissolved in 100mL of water and added dropwise over a fifteen minute period, The mixture was stirred for 4.5 hours, diluted with 1100 mL $CH_2Cl_2$, and filtered to remove insoluble solids. The filtrate was washed with two 500 mL portions of saturated brine, dried over anhydrous $Na_2SO_4$, and concentrated to dryness on a rotary evaporator to obtain 4′, 5′-dihydro-4,8-dimethyl-5′-hydroxypsoralen as a brown solid (22.33 g, 0.096 mol). All of this solid was heated on a steam bath for two hours with 85% $H_3PO_4$ (384 mL) and the brown solution was added to ca. 2 L of ice and water. Filtration yielded a brown solid, which was washed with several portions of $H_2O$, and dried (80° C., 1 mm) to obtain a crude product (18.90 g, 0.0882 mol, 88%). All of the crude product, dissolved in $CHCl_3$(HPLC grade, 900 mL), was placed on a column of alumina (1890 g, Fisher A-540). Elution was continued with $CHCl_3$ and fractions (225 mL) were monitored by TLC. Pure 4,8-dimethylpsoralen (Rf≅0.47) appeared in fraction 14 and in subsequent fractions up to number 30, in which low Rf impurities appeared on TLC. Concentration of fractions 14 through 29, using a rotary evaporator, gave 4,8-dimethylpsoralen (12.8 g, 0.0597 mol, 60%), mp 203°–204° C. (lit. mp 206° C.).

4-Methyl-8-bromomethylpsoralen. 4,8-Dimethylpsoralen (5.50 g, 25.7 mmol) dissolved in 550 mL of boiling $CCl_4$. To this boiling solution was added N-bromosuccinimide (4.57 g, 25.7 mmol) and dibenzoyl peroxide (0.622 g, 2.57 mmol) and the mixture was refluxed for four hours while being monitored with moist KI starch paper. The boiling mixture was filtered and the hot filtrate was allowed to cool and held at 0° C. for 48 hours. Yellow crystals were collected on a filter, taken up in 400 ml $CHCl_3$ and extracted with four 400-ml portions of water. The $CHCl_3$ solution was dried over anhydrous $MgSO_4$ and concentrated with a rotary evaporator to give 4-methyl-8-bromomethylpsoralen (4.315 g, 14.72 mmol, 57%), mp 194°–196° C. Sublimation in vacuo gave an analytical sample, mp 193.5°–195° C.

Anal. Calcd for $C_{13}H_9O_3Br$: C, 53.26; H, 3.09; Br, 27.27, Found: C, 53.00; H, 2.85; Br, 27.05.

8-Phthalimidomethyl-4-methylpsoralen. A mixture of 4-methyl-8-bromomethylpsoralen (1.000g, 3,411 mmol) and potassium phthalimide (0.758 g, 4.09 mmol) in 80 mL dimethylformamide was heated to 100° C. to dissolve the potassium phthalimide, and kept at that temperature for 10.5 hours. The solution was poured into 230 mL of water, and a white precipitate was collected by filtration, washed twice with water, and dried to constant weight (80° C., 1 mmHg) to give a crude product (1.047 g, 2.91 mmol, 86%), mp 217.5°–218° C. Recrystallization of that material (0.560 g, 1.56 mmol) from 45 mL of absolute ethanol gave an analytical sample (0.357 g, 0.99 mmol, 55%), mp 223.5°–224.5° C.

Anal. Calcd for $C_{21}H_{13}O_5N$: C, 70.19; H,3.65; N, 3.90, Found: C, 69.97; H, 3.89; N, 3.76.

4-Methyl-8-aminomethylpsoralen. A mixture of 8-phthalimidomethyl-4-methylpsoralen (5.90 g, 16.4 mmol), glacial acetic acid (20.5 mL, 359 mmol), and 85% hydrazine hydrate (7.50 mL, 131 mmol) in 708 mL of 95% ethanol was brought to a boil, whereupon all reagents went into solution, and refluxed for twelve hours. A TLC monitor of this reaction, on a smaller scale, indicated that a four-hour reflux period is sufficient. The solution was concentrated on the rotary evaporator to a viscous gum and 1F HCl (500 mL) was added, followed by enough $NaHCO_3$(s) to make a solution of ca. pH=8. That mixture was extracted with three 500 mL portions of $CHCl_3$ which were combined, dried over anhydrous $Na_2SO_4$ and concentrated to obtain a crude product (3.215 g, 14.03 mmol, 86%), mp 151°–154° C. That material (3.127 g, 13.64 mmol) was recrystallized from a benzene: ligroin (EK-P 1628)::80 ml:40 ml, solvent mixture to obtain pure 4-methyl-8-aminomethylpsoralen (1.61 g, 7.02 mmol, 44%), mp 154°–156° C.

Anal. Calcd for $C_{13}H_{11}O_3N$: C, 68.11; H, 4.84; N, 6.11, Found: C, 68.23; H, 5.07; N, 5.87.

4-Ethyl-8-aminomethylpsoralen. In the same manner as given in the foregoing, but starting from 4-ethyl-8-methylpsoralen in Step 4 or from 7-allyloxy-4-ethyl-8-methylcoumarin in Step 2, the title compound is produced.

4-Propyl-8-aminomethylpsoralen. In the same manner as given in the foregoing, but starting from 4-propyl-8-methylpsoralen in Step 4 or from 7-allyloxy-4- propyl-8-methylcoumarin in Step 2, the title compound is produced.

4-Methyl-8-aminoethylpsoralen. In the same manner as given in the foregoing, but starting from 4-methyl-8-ethylpsoralen in Step 4 or from 7-allyloxy-4-methyl-8-ethylcoumarin in Step 2, the title compound is produced.

In the same manner as given in the foregoing, other variations in selection of starting materials are productive of still other 4-loweralkyl-8-aminoloweralkylpsoralens, within the scope of the invention, in which one or both of the loweralkyl groups are varied. As used herein, the term loweralkyl" comprehends such straight or branched radicals or groups having one to eight carbon atoms, preferably one to four carbon atoms, inclusive, such as methyl, ethyl, propyl, isopropyl, butyl, and the like.

The 8-aminomethylpsoralen was made in the same manner, starting from 8-methylpsoralen, a known compound, for comparison purposes. The final step of its preparation follows:

8-Aminomethylpsoralen. A mixture of 8-phthalimidomethylpsoralen (0.250 g, 0.724 mmol), 95% ethanol (31 mL), glacial acetic acid (0.66 mL, 11.6 mmol), and 85% hydrazine hydrate (0.33 mL, 5.79 mmol) was refluxed with stirring (magnetic) until all of the phthalimidopsoralen had dissolved and until a TLC monitor showed the absence of starting material (ca. 3¾hours). The solution was concentration in vacuo to a viscous yellow liquid, which was acidified with 1 N aq. HCl (27 mL) and filtered to remove a precipitate, which was washed with two portions (7 mL) of 1 N aq. HCl. Solid $NaHCO_3$ was added to the combined filtrate and washes until their pH reached ca. 8 and that solution was extracted with five portions (25 mL) of $CHCl_3$. The $CHCl_3$ extracts were combined, dried ($Na_2SO_4$), and evaporated in vacuo to obtain 8aminomethylpsoralen (0.1152 g, 74%). Sublimation (130° C., 0.500 mm) of a portion gave a pure sample (52.5% recovery, 39% yield, 27% overall yield from 8-bromomethylpsoralen), mp 147°–150° C. A further purified sample melts at 156.8°–157.7° C. Structure is confirmed by NMR (CD $Cl_3$).

PHARMACOLOGY

The biophotosensitization activity of the compounds of the present invention was determined by visual grading of erythemal response according to a modification of the procedure of Pathak and Fitzpatrick, J. Invest. Dermatol. 32, 509–518 (1959), entitled "Bioassay of Natural and Synthetic Furocoumarins (Psoralens)". (The psoralens are of course "linear" isomers of the furocoumarin family.) According to this bioassay of photosensitizing potency, erythema production on albino guinea pig skin is measured visually and the response accorded a gradation definition according to 0, ∓, 1, 2, 3, and 4 scale. The modification employed involved variation of the time between administration of the test compound and exposure to ultraviolet light, thereby enabling measurement of times of onset and decline of the induced photosensitivity effect.

PROTOCOLS

Topical: Each drug is tested topically at a concentration of one percent (1%) in ethanolic solution. Test sites of one square centimeter of skin each receive one-tenth milliliter of a particular selected test solution thirty minutes prior to exposure to three joules of ultraviolet "A" radiation. Three species of fifteen in each group of guinea pigs are tested with each product to arrive at an average response designated "Reaction Intensity," which is determined by observation and grading 24 hours and 48 hours after administration.

Oral: Each drug is tested orally by administering a dosage of forty (40) mgm/kgm of body weight to groups of fifteen guinea pigs. The appropriate dosage for each animal is packed into a gelatin capsule and placed far back in the animal's pharynx. Swallowing is assisted by syringe delivery of three milliliters of water. The animals are not allowed to eat or drink six hours before and after administration of each product. The exposure to ultraviolet "A" radiation is at a dose of four joules per square centimeter at different times after administration, e.g., 10, 20, 30, 45, 60, 90, 120, 180, 240 minutes after administration. Readings and evaluations are carried out 48 hours post ingestion. When a particular product is exceptionally active in the test, the per os dosage may of course be halved or otherwise reduced.

Gradation: Responses are graded as follows:

0 No response; ±faint erythema; 1+ erythema; 2+ erythema and slight edema; 3+ erythema and intense edema; and 4+ vesiculobullous reaction.

RESULTS

The compounds of the invention show erythematic topical activity as read at both 24 and 48 hours. They show oral activity as read at 48 hours which is outstanding, with high maxima, early onset, and rapid decline in photosensitizing effect. The compound 4-methyl-8-aminomethylpsoralen is particularly outstanding, dropping off to no response at 180 minutes, with an early onset of only 10 minutes, reaching a vesicubullous reaction height at only 45 minutes, and dropping off to gradation 1+ at 120 minutes. It is superior in maintaining photosensitizing maximum and in rapidity of decline from maximum when compared with 4'-aminomethyl-4',5',8-trimethylpsoralen, and in all respects superior to the control methoxsalen (8-methoxypsoralen) which moreover does not show a rapid decline, exhibiting a 2+ rating after 240 minutes. In contrast, the 8-aminomethylpsoralen (made by identical procedure from 8-methylpsoralen) shows essentially no photosensitizing response orally, although it exhibits a 1+, 1+ topical response at 24 and 48 hours. The compounds of the invention show no oral toxicity, no animals dying at any of the dosage levels tested. In contrast, the compound 4'-aminomethyl-4,5',8-trimethylpsoralen shows a high order of oral toxicity, a large number of the animals receiving 40 mgm/kgm thereof dying during the period of their observation, the LD50 for that particular compound apparently being much less than this dosage level.

It is to be understood that the invention is not to be limited to the exact details of operation or exact compounds, compositions, methods, or procedures shown and described, as obvious modifications and equivalents will be apparent to one skilled in the art.

I claim:

1. 4-loweralkyl-8-primaryaminoloweralkypsoralen.

2. A compound of claim 1 which is 4-loweralkyl-8-aminomethylpsoralen.

3. A compound of claim 1 which is 4-methyl-8-aminomethylpsoralen.

4. A pharmaceutical composition suitable for use in effecting photochemical sensitivity on the skin of a mammal comprising a photo-sensitizing amount of a compound of claim 1 and a pharmaceutical carrier therefor.

5. The composition of claim 4, wherein the compound is 4-loweralkyl-8-aminomethylpsoralen.

6. The composition of claim 4, wherein the compound is 4-methyl-8-aminomethylpsoralen.

7. The method of effecting photochemical sensitivity on the skin of a mammal comprising the step of orally or topically administering to the said mammal an effective photosensitizing dose of a compound of claim 1.

8. The method of claim 7 wherein the compound is 4-loweralkyl-8-aminomethylpsoralen.

9. The method of claim 7 wherein the compound is 4-methyl-8-aminomethylpsoralen.

* * * * *

UNITED STATES PATENT AND TRADEMARK OFFICE
CERTIFICATE OF CORRECTION

PATENT NO. : 4,269,851
DATED : May 26, 1981
INVENTOR(S) : Kurt D. Kaufman

It is certified that error appears in the above—identified patent and that said Letters Patent is hereby corrected as shown below:

[56] References Cited, under OTHER PUBLICATIONS, line 2; "Comet." should read -- Cosmet. -- (original document)

Col. 2, lines 46 & 47; "8-methox-ypsoralen" (incorrectly hyphenated) should read -- 8-methoxypsoralen --

Col. 4, lines 5 & 6; "4,8-Dimethylp-soralen" (incorrectly hyphenated) should read -- 4,8-Dimethylpsoralen --

Col. 5, line 29; "concentration" should read -- concentrated --

Col. 5, line 37; "8aminomethylpsoralen" should read -- 8-aminomethylpsoralen --

Col. 6, line 61; "-8-primaryaminoloweralkypsoralen." should read -- -8-primaryaminoloweralkylpsoralen. --

Col. 6, line 68; "photo-sensitizing" delete the hyphen "-", should read -- photosensitizing --

Signed and Sealed this

Seventeenth Day of November 1981

[SEAL]

Attest:

GERALD J. MOSSINGHOFF

*Attesting Officer*   *Commissioner of Patents and Trademarks*